(12) United States Patent
Takahashi

(10) Patent No.: US 11,117,272 B2
(45) Date of Patent: Sep. 14, 2021

(54) VARIABLE-STIFFNESS ACTUATOR

(71) Applicant: OLYMPUS CORPORATION, Tokyo (JP)

(72) Inventor: Masaya Takahashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 226 days.

(21) Appl. No.: 16/392,681

(22) Filed: Apr. 24, 2019

(65) Prior Publication Data

US 2019/0248031 A1 Aug. 15, 2019

Related U.S. Application Data

(63) Continuation of application No. PCT/JP2016/082633, filed on Nov. 2, 2016.

(51) Int. Cl.
*B25J 19/06* (2006.01)
*F16C 1/00* (2006.01)
(Continued)

(52) U.S. Cl.
CPC ............ *B25J 19/068* (2013.01); *A61B 1/00* (2013.01); *A61B 1/0058* (2013.01); *F03G 7/06* (2013.01); *F16C 1/00* (2013.01); *G02B 23/24* (2013.01)

(58) Field of Classification Search
CPC .......... B25J 19/068; F16C 1/10; G02B 23/24; F03G 7/06; F03G 7/065; A61B 1/00; A61B 1/0058
See application file for complete search history.

(56) References Cited

U.S. PATENT DOCUMENTS 5,482,029 A 1/1996 Sekiguchi et al.
2006/0232669 A1 10/2006 Abadie et al.
(Continued)

FOREIGN PATENT DOCUMENTS

EP 2133566 A2 * 12/2009 ............ B25J 19/068
JP S58-101601 U 7/1983
(Continued)

OTHER PUBLICATIONS

Define hardness in science, Google Search, Feb. 18, 2021 (Year: 2021).*

(Continued)

*Primary Examiner* — Vinh Luong
(74) *Attorney, Agent, or Firm* — Scully, Scott, Murphy & Presser, P.C.

(57) ABSTRACT

A variable-stiffness actuator is to be installed into a flexible member and provide different degrees of stiffness to the flexible member. The actuator includes two hard members located apart from each other, and a shape-memory member connecting the hard members. The shape-memory member has a property of transitioning in phase between a first phase and a second phase. The shape-memory member is in a low stiffness state when in the first phase, and is in a high stiffness state when in the second phase. The actuator also includes a inducing member configured to cause a portion of the shape-memory member between the hard members to transition in phase between the first and second phases, and a urging member configured to urge the hard members in directions away from each other.

13 Claims, 5 Drawing Sheets

(51) Int. Cl.
*A61B 1/005* (2006.01)
*G02B 23/24* (2006.01)
*F03G 7/06* (2006.01)
*A61B 1/00* (2006.01)

(56) References Cited

U.S. PATENT DOCUMENTS

| | | | |
|---|---|---|---|
| 2006/0235458 A1 | 10/2006 | Belson | |
| 2017/0321666 A1* | 11/2017 | Morishima | A61B 1/0055 |
| 2020/0037852 A1* | 2/2020 | Takahashi | A61B 1/0058 |
| 2020/0260934 A1* | 8/2020 | Okita | A61B 1/015 |
| 2021/0000329 A1* | 1/2021 | Tezuka | A61B 1/00078 |

FOREIGN PATENT DOCUMENTS

| | | |
|---|---|---|
| JP | S58-101602 U | 7/1983 |
| JP | H01-247768 A | 10/1989 |
| JP | H05-91971 A | 4/1993 |
| JP | H6-70879 A | 3/1994 |
| JP | H10-127564 A | 5/1998 |
| JP | 2003-273192 A | 9/2003 |
| JP | 2008-538709 A | 11/2008 |
| WO | WO 2016/121060 A1 | 8/2016 |
| WO | WO 2016174741 A1 * 11/2016 ............ B25J 19/068 |

OTHER PUBLICATIONS

Stiffness, Wikipedia, Feb. 17, 2021 (Year: 2021).*
Define hard, Google Search, Feb. 17, 2021 (Year: 2021).*
Define stiffness, Google Search, Feb. 17, 2021 (Year: 2021).*
English translation of International Preliminary Report on Patentability dated May 16, 2019, together with the Written Opinion received in related International Application No. PCT/JP2016/082633.
International Search Report dated Jan. 31, 2017 issued in PCT/JP2016/082633.

* cited by examiner

VARIABLE-STIFFNESS ACTUATOR

CROSS-REFERENCE TO RELATED APPLICATIONS

This application is a Continuation Application of PCT Application No. PCT/JP2016/082633, filed Nov. 2, 2016, the entire contents of which are incorporated herein by reference.

BACKGROUND OF THE INVENTION

1. Field of the Invention

The present invention relates to a variable-stiffness actuator to be installed into a flexible member and provide different degrees of stiffness to the flexible member.

2. Description of the Related Art

Jpn. Pat. Appln. KOKAI Publication No. H5-91971 discloses an endoscope capable of providing different stiffness to a soft part of the insertion section. In this endoscope, a coil pipe extends along the soft part of the endoscope, a flexibility adjustment wire is inserted through the coil pipe, and an end of the flexibility adjustment wire is connected to the soft part of the endoscope through a separator. By pulling the flexibility adjustment wire, the coil pipe is compressed and hardened, thereby improving the stiffness of the soft part of the insertion section in which the flexibility adjustment wire extends.

BRIEF SUMMARY OF THE INVENTION

A variable-stiffness actuator is to be installed into a flexible member and provide different degrees of stiffness to the flexible member. The variable-stiffness actuator includes at least two hard members located apart from each other, and at least one shape-memory member connecting the hard members. The shape-memory member has a property of transitioning in phase between a first phase and a second phase. The shape-memory member is in a low stiffness state when the shape-memory member is in the first phase, and is in a high stiffness state, which is a state having a higher stiffness than the low stiffness state, when the shape-memory member is in the second phase. The variable-stiffness actuator also includes at least one inducing member configured to cause a portion of the shape-memory member located between the hard members to transition in phase between the first phase and the second phase, and at least one urging member configured to urge the hard members in directions away from each other.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment (Configuration)

Figure 1:
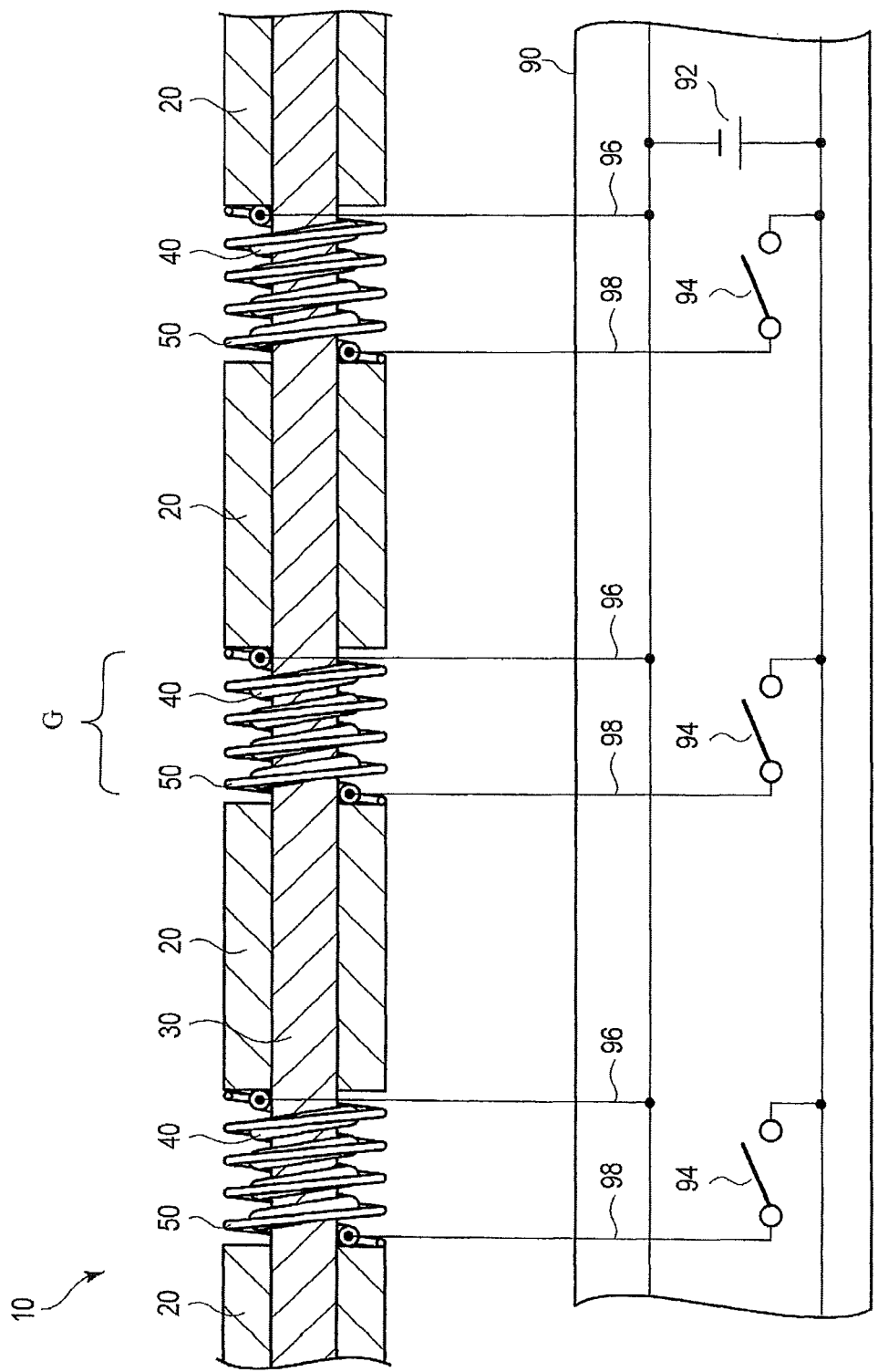
FIG. 1 shows a variable-stiffness apparatus according to a first embodiment.

FIG. 1 shows a variable-stiffness apparatus according to the first embodiment. As shown in FIG. 1, the variable-stiffness apparatus includes a variable-stiffness actuator 10 capable of taking different stiffness states and a controller 90 configured to control the stiffness state of the variable-stiffness actuator 10.

The variable-stiffness actuator 10 is to be installed into a flexible member and has a function of providing the flexible member with different degrees of stiffness through the feature capable of taking different stiffness states.

The variable-stiffness actuator 10 includes at least two, for example three or more hard members 20 located at a distance from one another, to define a gap G between the hard members 20, a single shape-memory member 30 connecting the hard members 20, at least one, for example two or more inducing members 40, and at least one, for example two or more urging members 50 configured to urge two adjacent hard members 20 in directions away from each other. In FIG. 1, four hard members 20, three inducing members 40, and three urging members 50 are depicted.

The shape-memory member 30 has a property of transitioning in phase between a first phase and a second phase, that is, undergoing phase transformation, depending on the temperature change. When the shape-memory member 30 is in the first phase, the shape-memory member 30 takes a low stiffness state, that is, exhibits a low modulus of elasticity, so as to provide a relatively low stiffness for the flexible member. When the shape-memory member 30 is in the second phase, the shape-memory member 30 takes a high-stiffness state, in which the stiffness is higher than that in the low-stiffness state, that is, exhibits a high modulus of elasticity, so as to provide a relatively high stiffness for the flexible member. The shape-memory member 30 has a tendency to easily deform according to external force in the low-stiffness state, and to return to the memorized shape that has been memorized beforehand against external force in the high-stiffness state. Here, the external force means a force capable of deforming the shape-memory member 30, and gravity is also regarded as part of the external force. The memorized shape may be, but is not limited to, a linear shape, for example.

The inducing member 40 has a function of causing a portion of the shape-memory member 30 located between two adjacent hard members 20 to transition in phase between the first phase and the second phase. The inducing member 40 has a capability of generating heat. The shape-memory member 30 has a property of transitioning in phase from the first phase to the second phase by receiving the heat generated by the inducing member 40.

The shape-memory member 30 is constituted by a shape-memory alloy, for example. The shape-memory alloy may be, but not limited to, an alloy including NiTi, for example. As the shape-memory alloy, NiTiCu that largely changes in stiffness change before and after phase transition is desirable, but of course any shape-memory alloy may be used as long as the stiffness changes depending on temperature change.

The shape-memory alloy constituting the shape-memory member 30 may be, for example, a shape-memory alloy that transitions in phase between a martensitic phase and an austenitic phase. In the martensitic phase, the shape-memory alloy is plastically deformed relatively easily by an external force. That is, the shape-memory alloy exhibits a low modulus of elasticity in the martensitic phase. On the other hand, in the austenitic phase, the shape-memory alloy is not easily deformed by an external force. Even when the shape-memory alloy is deformed by greater external force, it exhibits superelasticity and returns to its memorized shape when the greater external force is lost. That is, the shape-memory alloy exhibits a high modulus of elasticity in the austenitic phase.

Further, the shape-memory alloy constituting the shape-memory member 30 has a property of undergoing stress-induced martensitic transformation. That is, the shape-memory alloy has a property that the phase changes from the austenite phase to the martensite phase under stress.

The inducing member 40 is constituted from a conductive material, and has a property of generating heat in response to the supply of a current. The inducing member 40 may be constituted by, for example, a heating wire, namely, a conductive member with large electrical resistance.

Each of the hard members 20 is constituted by a cylindrical body. Each hard member 20 is constituted by, for example, a pipe of SUS (stainless steel material). Each hard member 20 is preferably constituted by a material having good thermal conductivity. The shape-memory member 30 has an elongated exterior shape. The shape-memory member 30 is constituted by, for example, a shape-memory alloy wire. The shape-memory member 30 extends through the inside of the hard member 20. Each hard member 20 is fixed to the shape-memory member 30. The fixation of each hard member 20 to the shape-memory member 30 may be done, for example, by brazing or caulking.

The inducing member 40 is constituted by a wire-like member. The inducing member 40 is constituted by, for example, a coil heater extending helically around the shape-memory member 30 between adjacent hard members 20. This configuration enables efficient conduction of heat generated by the inducing member 40 to the shape-memory member 30.

The urging member 50 is constituted by an elastic body. For example, the urging member 50 is constituted by a coil spring extending spirally around the inducing member 40 between adjacent hard members 20. The urging member 50 is disposed between the adjacent hard members 20 together with the inducing member 40. Therefore, the paired urging member 50 and inducing member 40 and the hard member 20 are alternately arranged. The urging member 50 is not limited to a coil spring. The urging member 50 need only have a function of urging two adjacent hard members 20 in directions away from each other. The urging member 50 may be constituted by another type of elastic body, for example, a rubber pipe or the like.

Both the coil heater constituting the inducing member 40 and the coil spring constituting the urging member 50 have a property of flexibly and elastically deforming. These structures are free from concern for breakage, even if they are bent.

As shown in FIG. 1, the controller 90 includes a power source 92 and switches 94 of the same number as the inducing members 40. An end of the power source 92 is electrically connected to ends of the inducing members 40 by a wire 96. The other end of the power source 92 is electrically connected to the other ends of the inducing members 40 through the switches 94 by a wire 98. The controller 90 supplies a current to each inducing member 40 according to an ON operation, namely a closing operation of each switch 94, and stops the supply of the current to each inducing member 40 in accordance with an OFF operation, namely an opening operation of each switch 94. Each inducing member 40 generates heat in response to the supply of current.

The variable-stiffness actuator 10 is into the flexible member without restricting both ends of the shape-memory member 30. For example, the variable-stiffness actuator 10 is arranged with a small gap in a limited space of the flexible member so that one or both ends of the shape-memory member 30 are a free end or free ends. With such an arrangement, when the shape-memory member 30 undergoes phase transformation to contract, the shape-memory member 30 is prevented from being damaged by the strong contraction force of the shape-memory member 30 itself, so that a stable use can be expected.

Here, the limited space means a space just capable of containing the variable-stiffness actuator 10. Therefore, even a slight deformation of one of the variable-stiffness actuator 10 and the flexible member may cause a contact with the other, applying an external force to the other.

For example, the flexible member is a tube having an inner diameter slightly larger than the outer diameter of the variable-stiffness actuator 10, and the variable-stiffness actuator 10 may be arranged inside the tube. The arrangement is not limited to this; the flexible member only has to have a space slightly larger than the variable-stiffness actuator 10.

When the shape-memory member 30 is in the first phase, the variable-stiffness actuator 10 provides a relatively low stiffness to the flexible member, so as to be easily deformed according to the external force acting on the flexible member, namely the force capable of deforming the shape-memory member 30.

When the shape-memory member 30 is in the second phase, the variable-stiffness actuator 10 provides a relatively high stiffness to the flexible member, so as to exhibit a tendency to return to the memorized shape against the external force acting on the flexible member, namely the force capable of deforming the shape-memory member 30.

For example, the phase of the shape-memory member 30 is switched between the first and second phases by the controller 90, so that the stiffness of the flexible member is switched.

In addition to switching the stiffness, in a situation where the external force is exerted on the flexible member, the variable-stiffness actuator 10 also functions as a bidirectional actuator that switches the shape of the flexible member. In another situation where no external force is exerted on the flexible member but the flexible member is deformed in the first phase before the phase of the shape-memory member 20 is switched to the second phase, the variable-stiffness actuator 10 also functions as a unidirectional actuator that returns the shape of the flexible member to the original.

(Effect)

Next, the effect of changing the stiffness of the variable-stiffness actuator 10 according to the present embodiment will be described with reference to the drawings.

In the variable-stiffness actuator 10, portions of the hard members 20 always have a high stiffness and are relatively difficult to bend. A portion between the adjacent hard members 20 is easier to bend than the portions of the hard members 20, but the ease of bending varies depending on the state of the phase of the portion of the shape-memory member 30 near the hard members 20. Thus, it can be said that the portions of the hard members 20 are high flexural stiffness portions, whereas the portion between the adjacent hard members 20 is a variable flexural stiffness portion.

In the state shown in FIG. 1, no current is supplied to any of the inducing members 40. For this reason, the shape-memory member 30 is in the first phase, for example, the martensite phase, and is in a low stiffness state. The hard members 20 have higher stiffness than the shape-memory member 30. Therefore, in the variable-stiffness actuator 10 in the state of FIG. 1, the portions of the hard members 20 are relatively difficult to bend, whereas the portion between the adjacent hard members 20 is relatively easy to bend.

Figure 2:
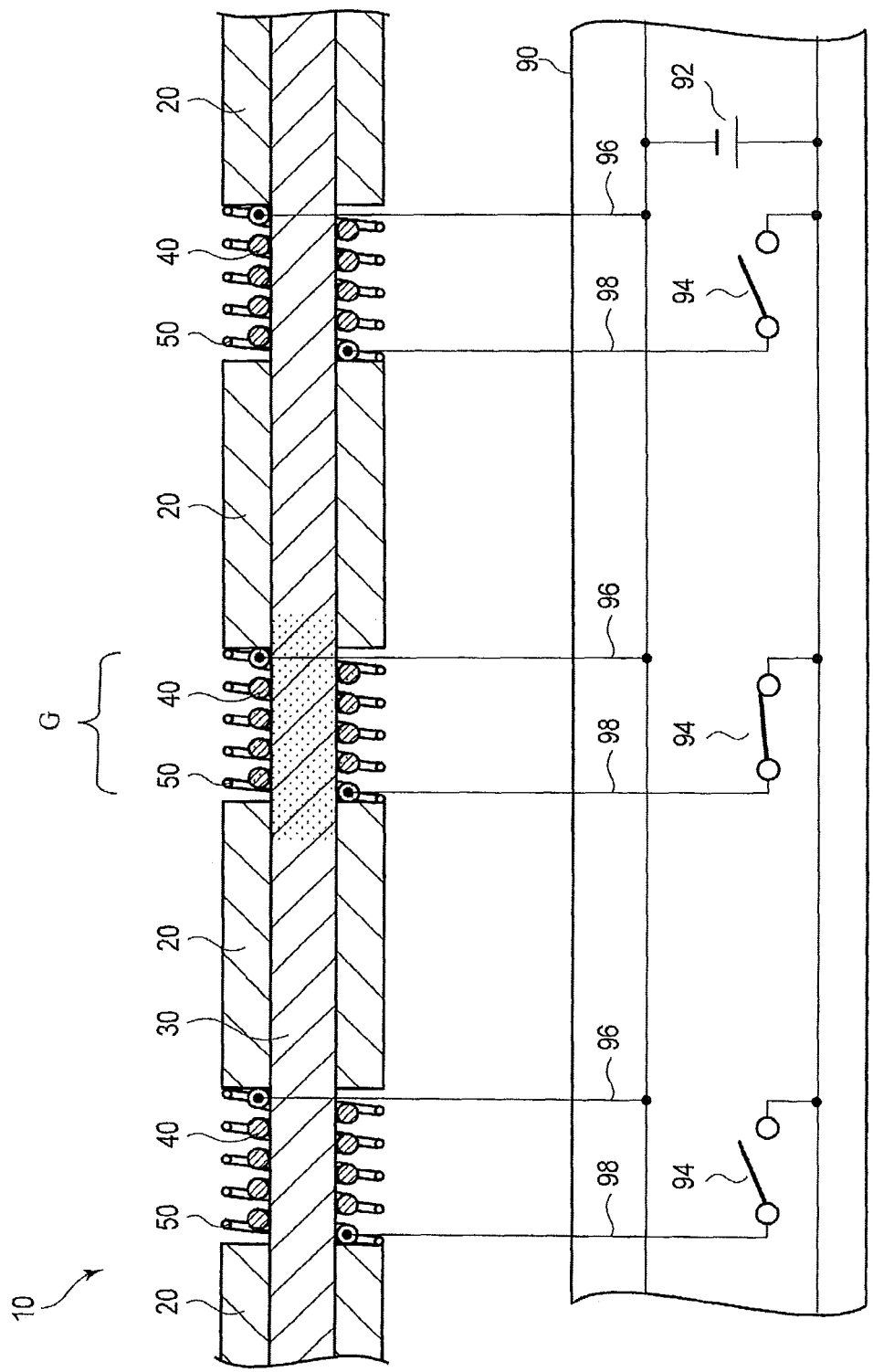
FIG. 2 shows a state in which a current is selectively supplied to an inducing member at the center of the figure in the variable-stiffness actuator shown in FIG. 1.

FIG. 2 shows a state in which a current is selectively supplied to the inducing member 40 at the center of FIG. 2. The central inducing member 40 in FIG. 2 generates heat in response to the supply of the current. The heat is efficiently transferred to a portion of the shape-memory member 30 located near the inducing member 40 in the center of FIG. 2. As a result, the portion of the shape-memory member 30 near the central inducing member 40 is heated and then the temperature rises. In FIG. 2, the heated portion of the shape-memory member 30 is indicated by dot shading. The heated portion of the shape-memory member 30 undergoes a phase transformation, so as to transition in phase from the first phase, for example the martensite phase, to the second phase, for example the austenite phase. As a result, the portion between the hard members 20 on both sides of the central inducing member 40 comes to have a high stiffness, so as to be more difficult to bend as compared with the state shown in FIG. 1.

In this way, selectively supplying a current to a specific inducing member 40 allows selectively increasing the stiffness of a portion between certain adjacent hard members 20 as compared to the state shown in FIG. 1.

Figure 3:
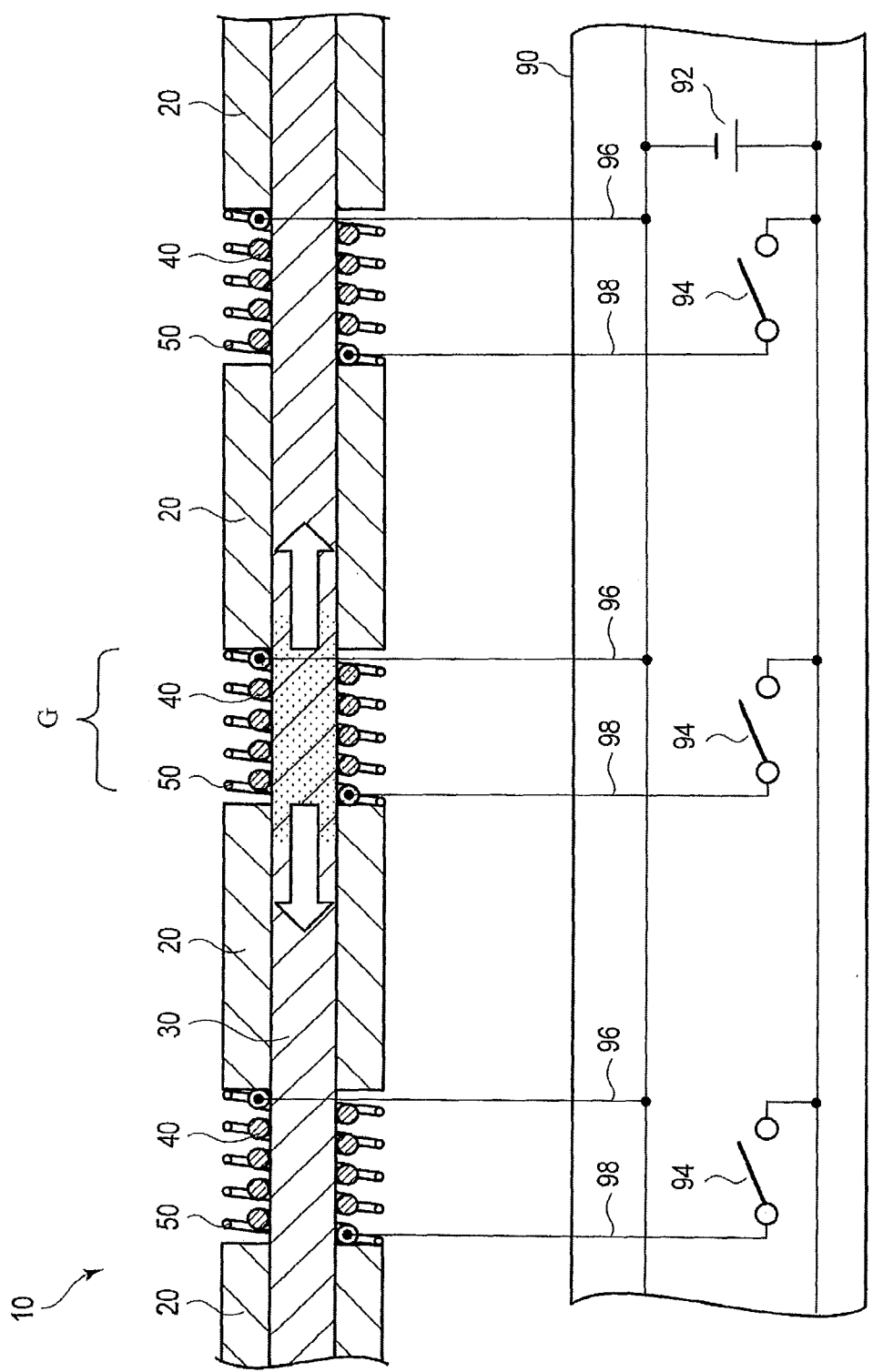
FIG. 3 shows a state in which the supply of the current to the inducing member at the center of the figure in the variable-stiffness actuator shown in FIG. 1 is stopped following the state shown in FIG. 2.

FIG. 3 shows a state in which the supply of the current to the central inducing member is stopped following the state shown in FIG. 2. Immediately after the supply of the current is stopped, the portion of the shape-memory member 30 around the central inducing member 40 is still in a state of having heat generated during the heating; it is therefore in the second phase, for example, the austenite phase, and a high stiffness state. Thereafter, due to natural heat dissipation, the temperature of the portion of the shape-memory member 30 around the central inducing member 40 drops. As the temperature drops, the portion of the shape-memory member 30 around the central inducing member 40 transitions in phase from the second phase, for example the austenite phase, to the first phase, for example the martensite phase. As a result, the portion between the hard members 20 on both sides of the central inducing member 40 comes to have a low stiffness, and becomes easier to bend as compared with the state shown in FIG. 2.

The hard member 20 preferably has high thermal conductivity to promote natural heat dissipation. Alternatively, a graphite sheet with good thermal conductivity may be put on the hard member 20 to promote heat conduction to the outside, thereby promoting natural heat dissipation. As a result, due to the temperature decrease, the time required for the shape-memory member 30 to return from the high-stiffness state to the low-stiffness state is shortened.

In addition, the adjacent hard members 20 fixed to the shape-memory member 30 are urged apart from each other by the urging members 50. For this reason, the portion of the shape-memory member 30 around the adjacent hard members 20 is subject to tensile stress as indicated by outlined arrows. As a result, in addition to the phase transformation due to the temperature drop, stress-induced martensitic transformation also occurs, in which phase transformation is induced by the action of stress. Therefore, the portion of the shape-memory member 30 in the second phase, for example the austenite phase transitions in phase to the first phase, for example the martensite phase, faster than in the state of receiving no tensile stress. That is, the urging member 50 shortens the time required to return the shape-memory member 30 from the high-stiffness state to the low-stiffness state.

(Advantage)

In the variable-stiffness actuator 10 of the present embodiment, selectively changing the presence or absence of supply of current to a specific inducing member 40 allows the stiffness of a portion between specific adjacent hard members 20 to be changed. This allows partially changing the stiffness of the flexible member into which the variable-stiffness actuator 10 is installed.

Second Embodiment (Configuration)

Figure 4:
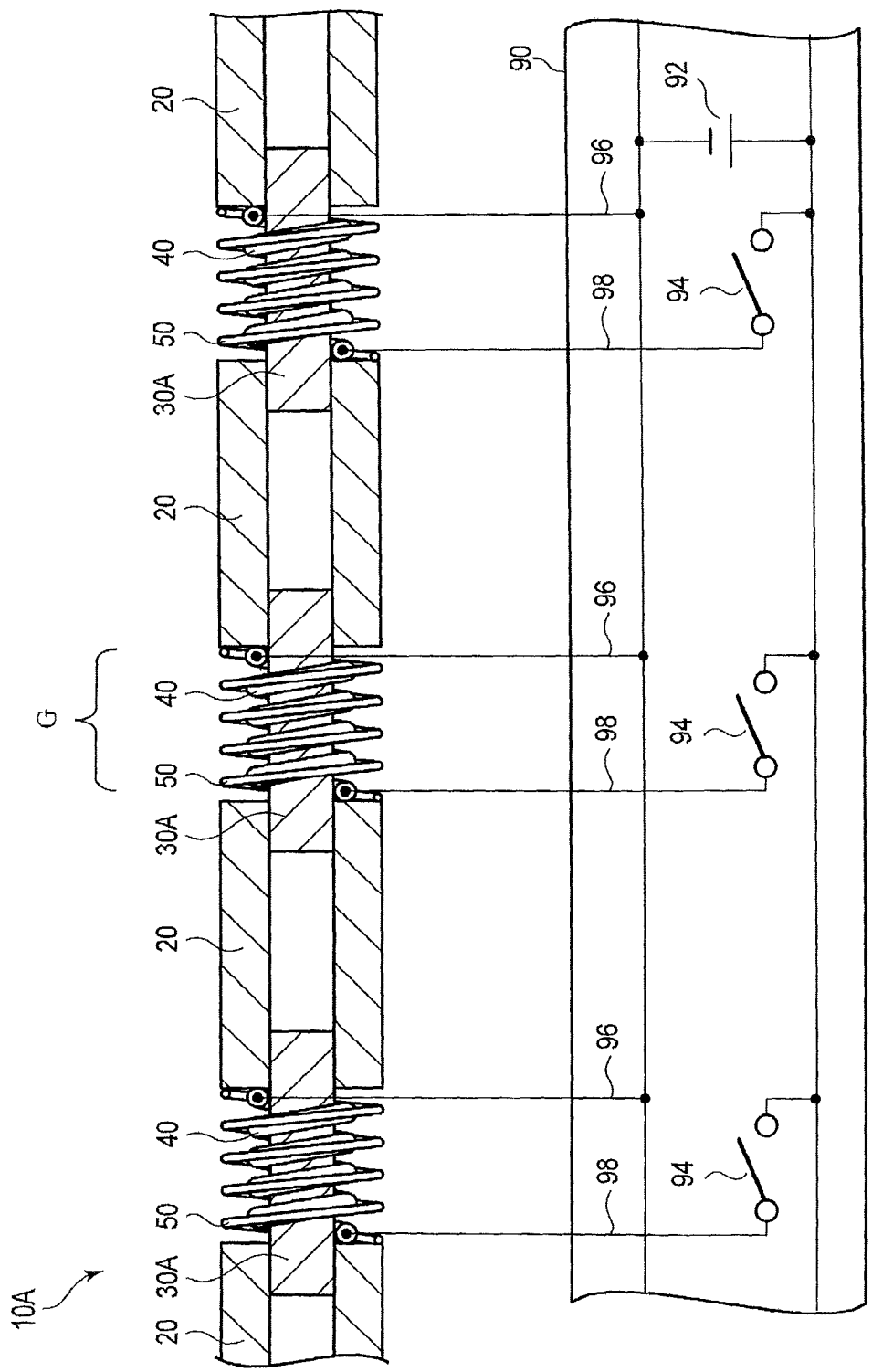
FIG. 4 shows a variable-stiffness apparatus according to a second embodiment.

FIG. 4 shows a variable-stiffness apparatus according to the second embodiment. In FIG. 4, the members identical to those shown in FIG. 1 are assigned the reference numerals identical to those shown in FIG. 1, and the detailed descriptions thereof are omitted. Hereinafter, an explanation will be provided with an emphasis on differences. That is, the points that are not mentioned below are the same as those of the first embodiment.

As shown in FIG. 4, the variable-stiffness apparatus according to the present embodiment includes a variable-stiffness actuator 10A capable of taking different stiffness states and a controller 90 configured to control the stiffness state of the variable-stiffness actuator 10A.

The variable-stiffness actuator 10A includes at least two, for example three or more hard members 20 located at a distance from one another, at least one, for example two or more shape-memory members 30A connecting hard members 20, at least one, for example two or more inducing members 40, and at least one, for example two or more urging members 50 configured to urge two adjacent hard members 20 in directions away from each other. In FIG. 4, four hard members 20, three shape-memory members 30A, three inducing members 40, and three urging members 50 are depicted.

Each shape-memory member 30A has a property of transitioning in phase between a first phase and a second phase. The properties of the shape-memory member 30A are similar to those of the shape-memory member 30 of the first embodiment described above.

Each shape-memory member 30A is constituted by, for example, a shape-memory alloy wire as well as the first embodiment. Each shape-memory member 30A extends partially inside the hard members 20. That is, each shape-memory member 30A is arranged to overlap with parts of the hard members 20. Each shape-memory member 30A is fixed to the hard members 20. The fixation between the hard members 20 and the shape-memory members 30 may be done, for example, by brazing or caulking.

(Effect)

Similar to the variable-stiffness actuator 10 of the first embodiment, also in the variable-stiffness actuator 10A of the present embodiment, selectively supplying a current to a specific inducing member 40 causes the shape-memory member 30A corresponding to the inducing member to be heated, which selectively increases the stiffness of the portion between the hard members 20 on both sides of the inducing member 40.

Furthermore, since the adjacent hard members 20 are urged apart from each other by the urging member 50, the heated shape-memory member 30A quickly returns from the high stiffness state to the low stiffness state after the stoppage of supply of the current to the inducing member 40 corresponding to the shape-memory member 30A.

(Advantage)

Also in the variable-stiffness actuator 10A of the present embodiment, selectively changing the presence or absence of current supply to a specific inducing member 40 allows the stiffness of a portion between specific adjacent hard members 20 to be changed. This allows partially changing the stiffness of the flexible member into which the variable-stiffness actuator 10A is installed.

Since adjacent hard members 20 are connected by separate shape-memory members 30A, the amount of heat required for the phase transformation of each shape-memory member 30A is small, and therefore, the power consumption necessary for changing the stiffness is small.

Third Embodiment (Configuration)

Figure 5:
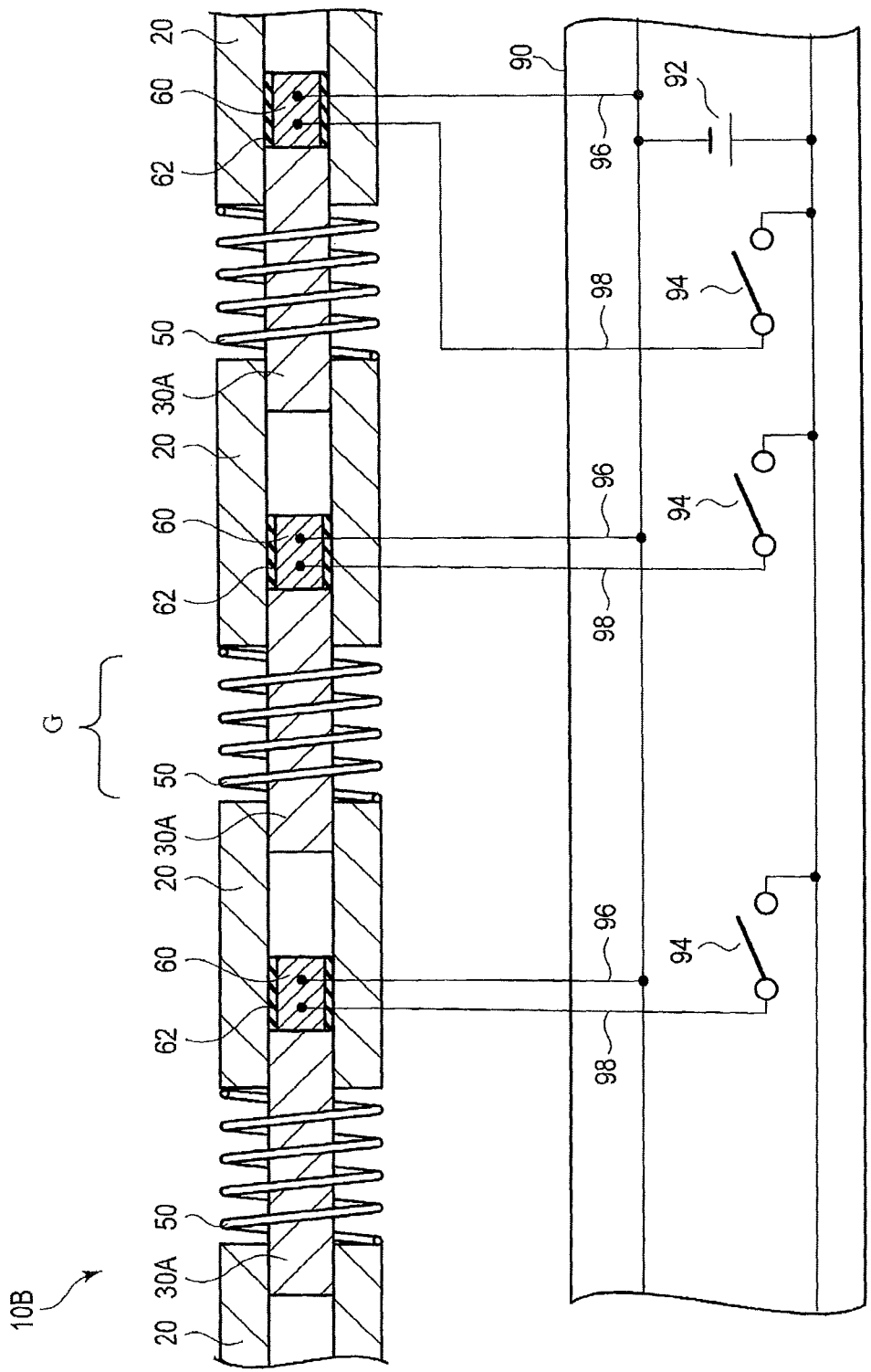
FIG. 5 shows a variable-stiffness apparatus according to a third embodiment.

FIG. 5 shows a variable-stiffness apparatus according to the third embodiment. In FIG. 5, the members identical to those shown in FIG. 4 are assigned the reference numerals identical to those shown in FIG. 1, and the detailed descriptions thereof are omitted. Hereinafter, an explanation will be provided with an emphasis on differences. That is, the points that are not mentioned below are the same as those of the second embodiment.

As shown in FIG. 5, the variable-stiffness apparatus according to the present embodiment includes a variable-stiffness actuator 10B capable of taking different stiffness states and a controller 90 configured to control the stiffness state of the variable-stiffness actuator 10B.

The variable-stiffness actuator 10B has a configuration different from the variable-stiffness actuator 10A of the second embodiment in which the inducing members 40 is replaced with inducing members 60. Each inducing member 60 is constituted by, for example, a ceramic heater. Each inducing member 60 is arranged, adjacent to each shape-memory member 30A, in the internal space of one of the hard members 20 connected to the shape-memory member 30A so as to overlap the hard member 20.

Between the inducing member 60 and the hard member 20, a heat insulating member 62 is provided so that the heat generated by the inducing member 60 is efficiently transferred to the shape-memory member 30A.

(Effect)

Similar to the variable-stiffness actuator 10 of the first embodiment, also in the variable-stiffness actuator 10B of the present embodiment, selectively supplying a current to a specific inducing member 40 causes the shape-memory member 30A corresponding to the inducing member to be heated, which selectively increases the stiffness of the portion between the hard members 20 on both sides of the inducing member 40.

Furthermore, since the adjacent hard members 20 are urged apart from each other by the urging member 50, the heated shape-memory member 30A quickly returns from the high stiffness state to the low stiffness state after the stoppage of supply of the current to the inducing member 40 corresponding to the shape-memory member 30A.

(Advantage)

Also in the variable-stiffness actuator 10B of the present embodiment, the stiffness of a portion between specific adjacent hard members 20 can be changed. This allows partially changing the stiffness of the flexible member into which the variable-stiffness actuator 10B is installed.

Since adjacent hard members 20 are connected by separate shape-memory members 30A, the power consumption necessary for changing the stiffness is small.

Compared with the first embodiment and the second embodiment, since the inducing members 40 between the adjacent hard members 20 are omitted, the stiffness of the portions between the adjacent hard members 20 is reduced.

Since the inducing members 60 are disposed in the inner spaces of the hard members 20, the inducing members 60 are not required to be flexible and elastic-deformed, unlike in the inducing members 40 of the first embodiment or the second embodiment. Therefore, an element that is not resistant to bending deformation can also be applied to the inducing members 60, and the degree of freedom of design is improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A variable-stiffness actuator comprising:
   at least one shape-memory member having a property of transitioning in phase between a first phase and a second phase, the at least one shape-memory member having a first bending stiffness when the at least one shape-memory member is in the first phase and having a second bending stiffness when the at least one shape-memory member is in the second phase, the second bending stiffness being greater than the first bending stiffness;
   at least two members connected to the at least one shape-memory member and located apart from each other to define a gap between the at least two members, the at least two members having a bending stiffness greater than a bending stiffness of a portion of the at least one shape memory member corresponding to the gap;
   at least one heater configured to cause the portion of the at least one shape-memory member corresponding to the gap to transition the at least one shape-memory member in phase between the first phase and the second phase; and at least one biasing material configured to bias the at least two members away from each other.

2. The variable-stiffness actuator according to claim 1, wherein the biasing material comprises an elastic body.

3. The variable-stiffness actuator according to claim 1, wherein the heater is arranged between the at least two members.

4. The variable-stiffness actuator according to claim 1, wherein the at least one shape-memory member is arranged so as to overlap portions of the at least two members.

5. The variable-stiffness actuator according to claim 4, wherein the heater is arranged so as to overlap one of the at least two members connected to the at least one shape-memory member.

6. A variable-stiffness actuator comprising:
a single shape-memory member having a property of transitioning in phase between a first phase and a second phase, the single shape-memory member having a first bending stiffness when the single shape-memory member is in the first phase and having a second bending stiffness when the single shape-memory member is in the second phase, the second bending stiffness being greater than the first bending stiffness;
three or more members connected to the single shape-memory member and located apart from each other to define a gap between each two adjacent members of the at three or more members, the three or more members having a bending stiffness greater than a portion of the single shape memory member corresponding to each gap;
a heater configured to cause at least portions of the single shape-memory member corresponding to each gap to transition the single shape-memory member in phase between the first phase and the second phase; and
a biasing material configured to bias each of the two adjacent members away from each other.

7. The variable-stiffness actuator according to claim 6, wherein each biasing material comprises an elastic body.

8. The variable-stiffness actuator according to claim 6, wherein each heater is arranged between each of the two adjacent members.

9. A variable-stiffness actuator comprising:
two or more shape-memory members located apart from one another, each of the two or more shape-memory members having a property of transitioning in phase between a first phase and a second phase, each of the two or more shape-memory members having a first bending stiffness when in the first phase and having a second bending stiffness when in the second phase, the second bending stiffness being greater than the first bending stiffness;
three or more members each connected to a shape-memory member of the two or more shape memory members, the three of more members being located apart from each other to define a gap between each two adjacent members of the at three or more members, the three or more members having a bending stiffness greater than a portion of the two or more shape memory members corresponding to each gap;
a heater configured to cause a portion of each of the two or more shape-memory members corresponding to each gap to transition in phase between the first phase and the second phase; and
a biasing material configured to bias each of the two adjacent members away from each other.

10. The variable-stiffness actuator according to claim 9, wherein each biasing material comprises an elastic body.

11. The variable-stiffness actuator according to claim 9, wherein each heater is arranged between each of the two adjacent members.

12. The variable-stiffness actuator according to claim 9, wherein each of the two or more shape-memory members is arranged to overlap portions of the two adjacent members.

13. The variable-stiffness actuator according to claim 12, wherein each heater is arranged to overlap one of the two adjacent members.

* * * * *